(12) United States Patent
Haller

(10) Patent No.: US 7,993,287 B2
(45) Date of Patent: Aug. 9, 2011

(54) ENDOSCOPIC WIRE GUIDE

(75) Inventor: Frederick B. Haller, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 571 days.

(21) Appl. No.: 11/713,948

(22) Filed: Mar. 5, 2007

(65) Prior Publication Data

US 2007/0208218 A1 Sep. 6, 2007

Related U.S. Application Data

(60) Provisional application No. 60/779,105, filed on Mar. 3, 2006.

(51) Int. Cl.
*A61B 1/00* (2006.01)
*A61M 25/00* (2006.01)

(52) U.S. Cl. .......................... 600/585; 600/104
(58) Field of Classification Search .................. 600/433, 600/434, 585, 104; 604/164.13
See application file for complete search history.

(56) References Cited

U.S. PATENT DOCUMENTS

| | | |
|---|---|---|
| 4,407,273 A | 10/1983 | Ouchi et al. |
| 4,841,949 A | 6/1989 | Shimizu et al. |
| 5,343,853 A | 9/1994 | Komi et al. |
| 5,386,818 A | 2/1995 | Schneebaum et al. |
| 5,707,344 A | 1/1998 | Nakazawa et al. |
| 5,820,546 A | 10/1998 | Ouchi |
| 5,899,850 A | 5/1999 | Ouchi |
| 5,921,971 A | 7/1999 | Agro et al. |
| 5,938,586 A | 8/1999 | Wilk et al. |
| 5,938,587 A | 8/1999 | Taylor et al. |
| 6,290,656 B1 * | 9/2001 | Boyle et al. ............... 600/585 |
| 6,827,683 B2 | 12/2004 | Otawara |
| 2002/0087100 A1 * | 7/2002 | Onuki et al. ............... 600/585 |
| 2002/0091303 A1 | 7/2002 | Ootawara et al. |
| 2004/0199088 A1 * | 10/2004 | Bakos et al. ............... 600/585 |
| 2005/0101836 A1 | 5/2005 | Onuki et al. |

FOREIGN PATENT DOCUMENTS

| | | |
|---|---|---|
| EP | 1 764 028 A1 | 3/2007 |
| WO | WO 99/29362 | 6/1999 |
| WO | WO 00/74565 A1 | 12/2000 |
| WO | WO 2006/004053 A1 | 1/2006 |
| WO | WO 2006/113465 A1 | 10/2006 |

OTHER PUBLICATIONS

International Search Report—PCT/US2007/005859 (Nov. 16, 2007).
International Search Report—PCT/US2007/005564 (Jan. 21, 2008).
International Search Report—PCT/US2007/005657 (Sep. 13, 2007).

* cited by examiner

*Primary Examiner* — Max Hindenburg
*Assistant Examiner* — Jonathan M Foreman
(74) *Attorney, Agent, or Firm* — Brinks Hofer Gilson & Lione

(57) ABSTRACT

An endoscopic wire guide apparatus for insertion through an insertion tube of an endoscope having an accessory port, the endoscope being configured for advancement into a patient. The apparatus comprises a wire guide disposed through the insertion tube for delivery into the patient. The wire guide has a distal portion and a proximal portion. The distal portion has a first diameter and the proximal portion has a second diameter less than the first diameter. The first diameter is more rigid than the second diameter. The second diameter is configured to allow the proximal portion to collapse when proximally extending through the accessory port of the endoscope and the distal portion extends at least partially beyond the distal end of the insertion tube.

19 Claims, 3 Drawing Sheets

ENDOSCOPIC WIRE GUIDE

CROSS-REFERENCE TO RELATED APPLICATIONS

This application claims the benefit of U.S. Provisional Application Ser. No. 60/779,105, filed on Mar. 3, 2006, entitled "ENDOSCOPIC WIRE GUIDE," the entire contents of which are incorporated herein by reference.

FIELD OF THE INVENTION

The present invention relates to medical devices, and more particularly, to endoscopic wire guides.

BACKGROUND OF THE INVENTION

Endoscopic devices have been commonly used for various procedures, typically in the abdominal area. Endoscopy is the examination and inspection of the interior of body organs, joints or cavities through an endoscope. Endoscopy allows physicians to peer through the body's passageways. An endoscopic procedure may be used to diagnose various conditions by close examination of internal organ and body structures and may also guide therapy and repair, such as the removal of torn cartilage from the bearing surfaces of a joint. A biopsy, a procedure involving tissue sampling for pathologic testing, may also be performed under endoscopic guidance. For example, endoscopic procedures include the following known procedures: gastroscopy, sigmoidoscopy and colonoscopy, esophago gastro duodenoscopy (EGD), endoscopic retrograde cholangiopancreatography (ERCP), and bronchoscopy.

The use of endoscopic treatments has recently increased for some diseases occurring in the gastrointestinal or pancreatobiliary duct systems. Endoscope systems are used frequently for diagnostic procedures, including contrast imaging of biliary or pancreatic ducts. Endoscopes are also used in procedures for retrieving gallstones that exist in the common bile duct and. elsewhere.

Typically, these treatments and procedures are performed in the pancreatic duct, bile duct, and the hepatic duct by positioning the distal end of an endoscope in the vicinity of the duodenal papilla. Once the endoscope is in place, a wire guide is delivered to the target anatomy so that other devices may be guided to a target location in the patient anatomy. This is accomplished by disposing the wire guide through the working channel of the endoscope to the target location. Another device, such as a catheter, may then be disposed over the wire guide through the working channel of the endoscope as needed.

Although many current endoscopic apparatus are adequate, improvements may be made. For example, when a wire guide is disposed through a working channel of an endoscope, the distal portion thereof is placed at a target location in the patient anatomy and the proximal portion normally extends out of the accessory port of the endoscope. Due to the rigid structure of the wire guide and the typical design of the accessory port, the proximal portion of the wire guide typically extends out of the accessory port at an inconvenient position or angle. In many situations, the proximal portion extends relatively horizontal, upward, or in the way of a clinician. This creates a risk of undesirable contact with the clinician. That is, clinicians experience challenges in avoiding inadvertent contact with the proximal portion or end of the wire guide during use, as the wire guide proximally extends through an accessory port of an endoscope.

Thus, there is a need to reduce the risk of undesirable contact with an endoscope wire guide during endoscopy as the wire guide proximally extends through an accessory port of an endoscope.

BRIEF SUMMARY OF THE INVENTION

The present invention generally provides an endoscopic wire guide that solves the challenges mentioned above. The present invention provides a way of lessening the risk of inadvertent contact of the clinician with an endoscopic wire guide during endoscopy as the wire guide proximally extends through an accessory port of an endoscope. As a result, undesirable movement of the wire guide relative to a target location in the patient anatomy is avoided.

In one embodiment, the present invention provides an endoscopic wire guide apparatus for insertion through an insertion tube of an endoscope having an accessory port. The endoscope is configured for advancement into a patient. The apparatus comprises a wire guide that is disposed through the insertion tube for delivery in the patient. The wire guide has a distal portion extending to a distal end and a proximal portion extending from the distal portion to a proximal end. The distal portion has a first segment and the proximal portion having a second segment less rigid than the first segment. The second segment has a reduced diameter and being configured to allow the proximal portion to collapse when proximally extending through the accessory port of the endoscope.

In another embodiment, the wire guide apparatus comprises a second segment made of material having increased flexibility. The second segment is configured to allow the proximal portion to collapse when proximally extending through the accessory port of the endoscope.

In another example, the present invention provides a method of delivering a wire guide apparatus for insertion through an insertion tube of an endoscope having an accessory port. The endoscope is configured for advancement into a patient. The method comprises inserting the endoscope to a target location in a patient anatomy. The method further comprises advancing a wire guide distally through the accessory port of the endoscope. The wire guide has a distal portion extending to a distal end and a proximal portion extending from the distal portion to a proximal end. The distal portion has a first segment and the proximal portion having a second segment less rigid than the first segment. The second segment is configured to allow the proximal portion to collapse at the second segment when proximally extending through the accessory port of the endoscope. The method further comprises aligning the second segment of the wire guide longitudinally adjacent the accessory port. The second segment extends distally therefrom to allow the proximal portion of the wire guide to droop relative to gravity;

Further objects, features, and advantages of the present invention will become apparent from consideration of the following description and the appended claims when taken in connection with the accompanying drawings.

DETAILED DESCRIPTION OF THE INVENTION

Embodiments of the present invention provide an improved wire guide for reducing the risk of inadvertent contact with the wire guide by the clinician during endoscopy as the wire guide proximally extends through an accessory port of an endoscope. In one embodiment, an endoscopic wire guide apparatus comprises a wire guide having distal and proximal portions. The distal portion comprises a first segment and the proximal portion comprises a second segment that is less rigid than the first segment. The second segment allows the proximal portion to droop or bend when the wire guide extends proximally through an accessory port of the endoscope. As a result, a clinician will less likely inadvertently contact the wire guide, thereby avoiding undesirable movement of the wire guide at a target location in the patient anatomy.

Figure 1:
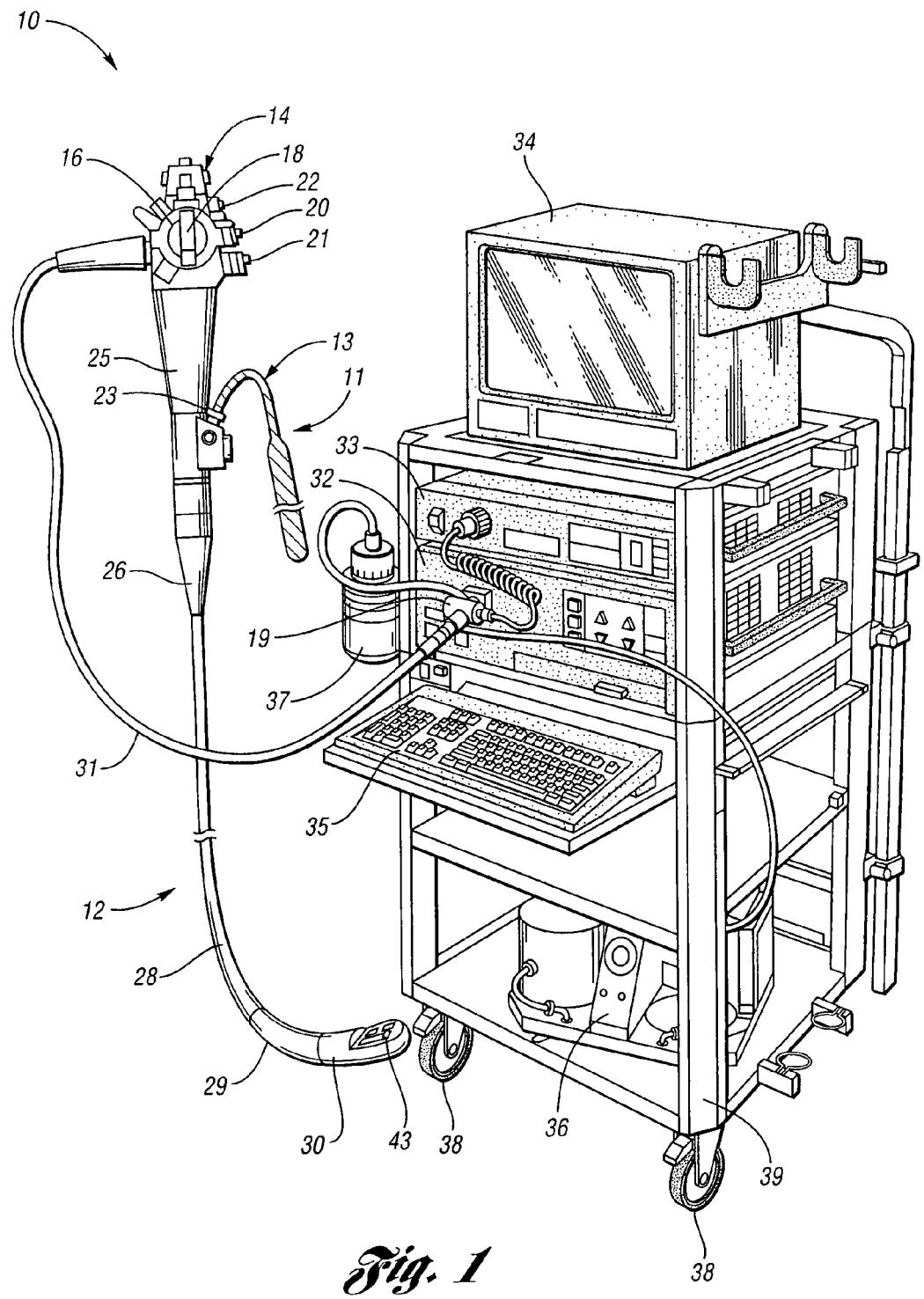
FIG. 1 is a perspective view of an endoscopic system comprising an endoscopic wire guide in accordance with one embodiment of the present invention.

FIG. 1 illustrates an endoscopic system 10 comprising an endoscopic wire guide and an endoscope 11 in accordance with one embodiment of the present invention. In this embodiment, the endoscope 11 comprises an insertion tube 12 to be inserted into a body cavity for various endoscopic procedures including gastroscopy, sigmoidoscopy and colonoscopy, esophago gastro duodenoscopy (EGD), endoscopic retrograde cholangiopancreatography (ERCP), and bronchoscopy. The insertion tube 12 comprises a plurality of accessory channels through which endoscopic components, e.g., a wire guide, may be disposed. In one embodiment, endoscopic components disposed in one of the channels may include one embodiment of an improved wire guide as described in greater detail below.

Figure 2:
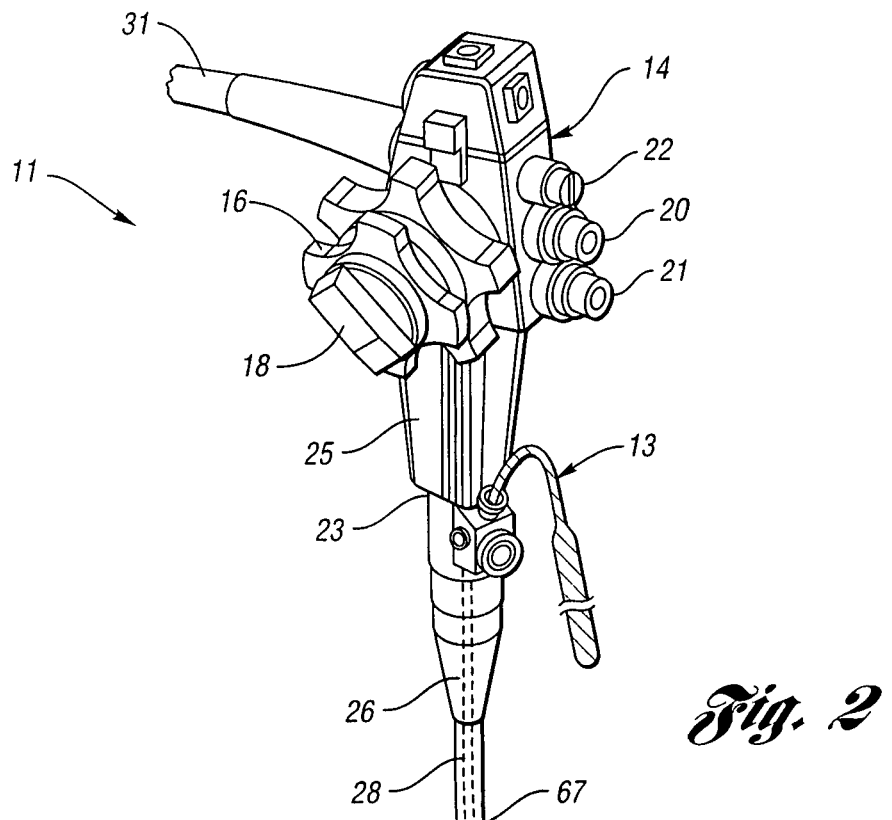
FIG. 2 is another perspective view of the endoscopic wire guide depicted in FIG. 1.

FIGS. 1 and 2 illustrate the system 10 comprising an endoscopic wire guide 13 disposed through an accessory port 23. As shown, the wire guide 13 extends proximally from the insertion tube 12 through the accessory port 23. As the wire guide 13 extends through and out of the accessory port 23, the wire guide 13 folds downwardly. As a result, a clinician is less likely to inadvertently contact the wire guide 13 during an endoscopy procedure, thereby lessening the risk of undesirable movement of the wire guide at a target location in a patient anatomy.

As shown in FIGS. 1 and 2, the endoscope 11 further includes a control system 14 that is in mechanical and fluid communication with the insertion tube 12. The control system 14 is configured to control the insertion tube 12 and endoscopic components disposed therein. As shown, the control system 14 includes first and second control knobs 16, 18. The control knobs 16, 18 are configured to be in mechanical communication with the insertion tube 12. The control knobs 16, 18 allow the physician to control and guide, by known means, the insertion tube 12 through vessels and cavities of a patient.

The control system 14 further includes valve switches (e.g., suction valve 20, air/water valve 21, camera valve 22), each of which are in communication with one of the channels of the insertion tube 12. For example, the suction valve switch 20, when activated, allows a vacuum from a suction source through a suction channel for suctioning unwanted plaque and debris from the patient. In one example, the distal end of the insertion tube 12 is inserted, rectally or orally, to a predetermined target location within a patient anatomy. Introduction of the insertion tube 12 may be rectally or orally depending on the endoscopic procedure.

As mentioned above, the control system 14 further comprises the accessory port 23 through which the wire guide 13 is disposed. The accessory port 23 is in fluid communication with channel 67 which is formed through the insertion tube 12 so that an endoscopic component, e.g., a wire guide, may be disposed through the distal tip 30 of the endoscope 11.

In this embodiment, the insertion tube 12 comprises an operating portion 25 connected to the control system 14 and extending to an insertion portion protecting member 26. A control system 20 is connected to the operating portion 25 and is configured to control the insertion tube 12. In this embodiment, the insertion tube 12 is composed of components that include a flexible tube 28, a flexure 29 connected to the flexible tube 28, and an endoscope tip 30 connect to the flexure 29. A universal cord 31, on one end, is connected and in communication with the control system 20. On the other end, the cord 31 has a connector 19 attached thereto. The connector 19 is in communication with a light guide tube and electrical contact, and is connected to a light source apparatus 32 and an image processing apparatus 33 (external devices). These external devices may include a monitor 34, an input keyboard 35, a suction pump apparatus 36, an irrigation bottle 37, and other suitable apparatus that are installed on a rack 39 equipped with carriers 38.

Figure 3:
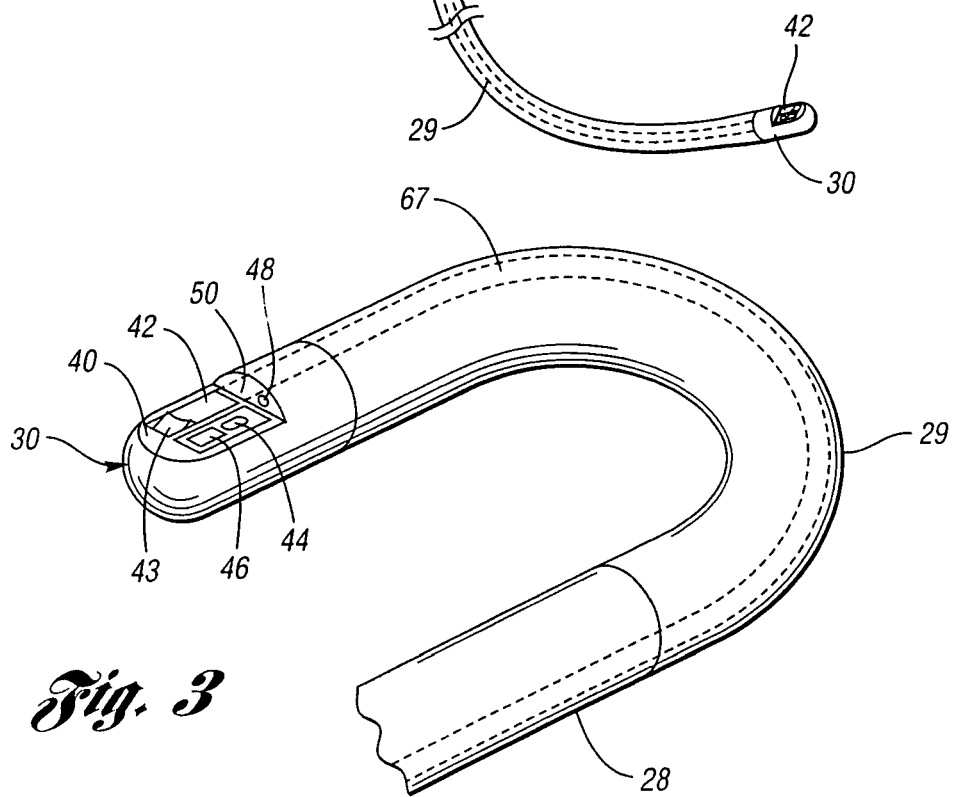
FIG. 3 is an elevated view of a distal end of the endoscope in accordance with one embodiment of the present invention.

As shown in FIG. 3, a cutout 40 is formed on the outer circumferential surface of the tip 30 in one example. In this embodiment, a channel opening 42 is formed on one side of the cutout 40, and an objective lens 44 and a light source 46 are disposed on another side of the cutout 40 for imaging. Both the objective lens 44 and the light source 46 are positioned adjacent to the channel opening 42. The tip 30 further comprises a nozzle 48 extending from a back wall surface 50 of the cutout 40. The nozzle 48 allows a stream of water, air, or the like to spray towards the outer surface of the objective lens 44 to clean the lens surface.

Figure 4:
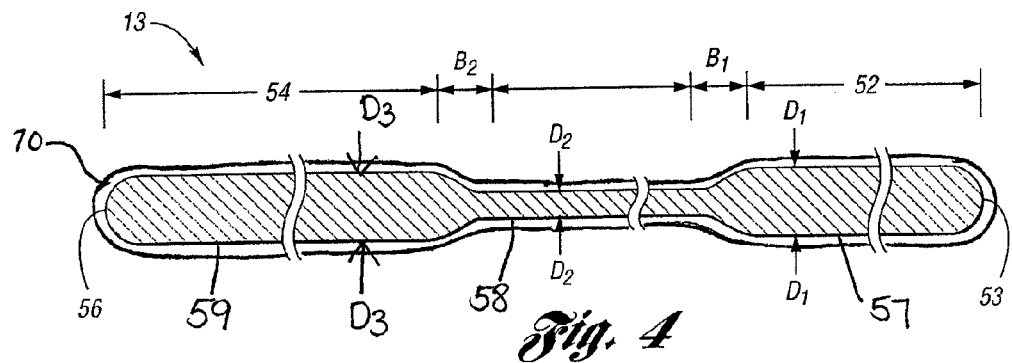
FIG. 4 is a side view of an endoscopic wire guide in accordance with one embodiment of the present invention.

FIG. 4 illustrates the wire guide 13 comprising a distal portion 52 having a distal end 53. As shown, the wire guide 13 further comprises a proximal portion 54 having a proximal end 56. In this embodiment, the distal portion 52 comprises a first segment 57 having a first diameter $D_1$ that extends along the entire length of the distal portion 52 to the proximal portion 54. In this embodiment, the proximal portion 54 comprises a first transition area $B_1$ that proximally tapers and extends to a second segment 58 having a second diameter $D_2$. Preferably, the second segment 58 is less rigid than the first segment 57 and is configured to allow the proximal portion 54 to droop relative to gravity when the second segment 58 proximally extends through the accessory port of the endoscope. In this embodiment, this is accomplished since the second diameter $D_2$ has a reduced diameter relative to the first diameter $D_1$. That is, the second diameter $D_2$ is less than the first diameter $D_1$. The second segment 58 extends from the first transition area $B_1$ along the proximal portion 54 to a second transition area $B_2$. As shown in FIG. 4, the second transition area $B_2$ flares and extends proximally to a third segment 59 having a third diameter $D_3$ greater than the second diameter $D_2$. In this embodiment, the third diameter $D_3$ is the first diameter $D_1$. As mentioned, the second segment 58 having the second diameter $D_2$ is configured to allow the wire guide 13 to droop downwardly due to gravity when proximally extending from the insertion tube 12 through the accessory port 23. Thus, a clinician may avoid inadvertent contact with the wire guide 13 during an endoscopy procedure.

However, it is understood that the proximal portion 54 may include merely the second segment 58 having only the second diameter $D_2$ and extending along the entire length of the proximal portion 54 without falling beyond the scope or spirit of the present invention.

In one example, the wire guide 13 has a total length of up to 225 centimeters (cm). Preferably, the total length is between about 185 cm and 225 cm. The distal portion may have a length of about 160 cm and 185 cm, as measured from the distal end 53 of the wire guide 13, and the second segment may have a length of about 5 to 15 cm, allowing drooping or folding along the second diameter $D_2$ when the proximal portion 54 extends from the accessory port 23 of the endoscope 11. The distal portion 52 extends at least partially beyond the tip 30 of the endoscope 11.

In this embodiment, the wire guide 13 may have an outer coating 70 disposed about the wire guide 13. As shown, the outer coating is disposed along the distal and proximal portions 52, 54 so that the wire guide has a constant outer diameter therealong. The outer coating may comprise polytetrafluoroethylene, polyethylene, polypropylene, perfluoroelastomer, fluoroelastomer, nitrile, neoprene, polyurethane, silicone, styrene-butadiene, rubber, or polyisobutylene or a mixture thereof.

Figure 5:
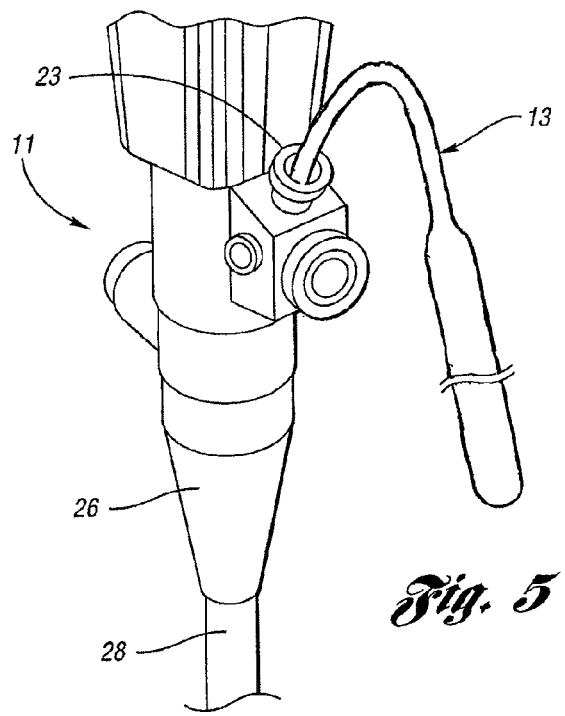
FIG. 5 is a partially enlarged view of the endoscopic wire guide of FIG. 3.

FIG. 5 depicts the wire guide 13 in FIG. 4 disposed within the insertion tube 12 of endoscope 11. As shown, the proximal portion 54 of the wire guide 13 extends through the accessory port 23 and droops downwardly. The configuration of the proximal portion 54 and the proximal diameter $D_2$ allows the wire guide to fold or bend downwardly when proximally extending from the insertion tube 12 through the accessory port 23 and the distal portion 52 extends at least partially beyond the tip 30 of the endoscope 11. As a result, a clinician is less likely to inadvertently contact the wire guide 13 during an endoscopy procedure, thereby avoiding undesirable movement of the wire guide at a target location in the patient anatomy.

Figure 6:
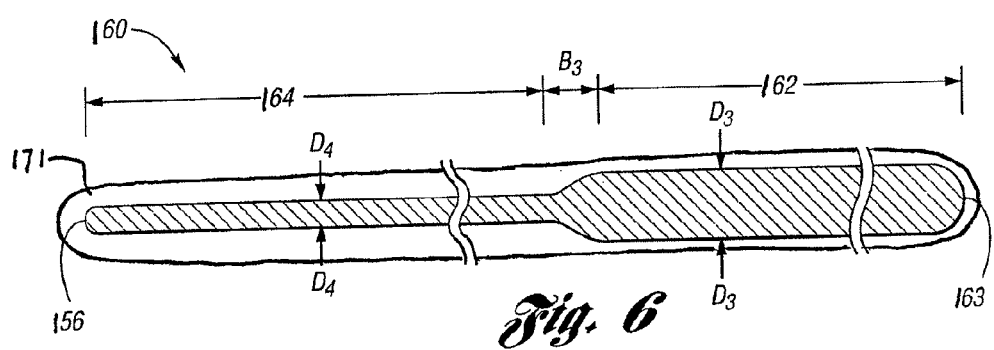
FIG. 6 is a side view of an endoscopic wire guide in accordance with another embodiment of the present invention.

FIG. 6 illustrates a wire guide 160 in accordance with another embodiment of the present invention. As shown, the wire guide 160 comprises a distal portion 160 having a distal end 163 and a proximal portion 164 having a proximal end 156. In this embodiment, the distal portion 162 has a distal diameter $D_3$ extending to a transition area $B_3$ along the entire length of the distal portion 162. The proximal portion 164 has a proximal diameter $D_4$ extending from the transition area $B_3$ to the proximal end 156 along the entire length of the proximal portion. As shown, the proximal diameter $D_4$ is reduced and less than the distal diameter $D_3$, thereby allowing the proximal portion 164 extending from the accessory port 23 of the endoscope 10 to bend or fold and the distal portion 162 extends at least partially beyond the tip 30 of the endoscope 11. As the embodiment described above, a clinician avoids inadvertent contact with the wire guide during an endoscopy procedure.

In another embodiment, the second segment is made of material having increased flexibility to allow the proximal portion to droop when proximally extending through the accessory port of the endoscope. In this embodiment, the material may be superelastic material or shape memory material having a transition temperature, e.g., nitinol.

In yet another example, the present invention comprises a method of delivering a wire guide apparatus for insertion through an insertion tube of an endoscope having an accessory port. The method comprises inserting the endoscope to a target location in a patient anatomy. This is accomplished by any medical procedure or any technique known in the art. The method further comprises advancing the wire guide distally through the accessory port of the endoscope. In this example, the wire guide has a distal portion extending to a distal end and a proximal portion extending from the distal portion to a proximal end. The distal portion has a first segment and the proximal portion has a second segment less rigid than the first segment as mentioned above. The second segment is configured to allow the proximal portion to collapse at the second segment when proximally extending through the accessory port of the endoscope.

The method further comprises aligning the second segment of the wire guide longitudinally adjacent the accessory port. The second segment extends distally from the accessory port to allow the proximal portion of the wire guide to droop relative to gravity.

While the present invention has been described in terms of preferred embodiments, it will be understood, of course, that the invention is not limited thereto since modifications may be made to those skilled in the art, particularly in light of the foregoing teachings.

The invention claimed is:

1. An endoscopic apparatus comprising:
    an insertion tube for an endoscope configured for advancement into a patient, the insertion tube having an accessory port, the insertion tube extending distally from the accessory port to a distal tip;
    a wire guide disposed through the insertion tube for delivery in the patient, the wire guide having a distal portion extending to a distal end and a proximal portion extending from the distal portion to a proximal end, the distal portion extending distally from the accessory port of the insertion tube in substantially the same direction as the distal tip of the insertion tube extends distally from the accessory port, the distal portion having a first segment and the proximal portion having a second segment and a third segment, the second segment being less rigid than the first segment, the second segment having a reduced diameter and extending proximally through the accessory port; the third segment extending proximally from the second segment to the proximal end of the wire guide; the second segment being located distant from the center of the wire guide; the second segment being configured to allow the third segment of the proximal portion to droop relative to gravity when the second segment proximally extends through the accessory port of the endoscope as the distal end of the distal portion extends distally.

2. The apparatus of claim 1 wherein the first segment has a first diameter and the second segment has a second diameter less than the first diameter to allow the proximal portion to collapse when proximally extending through the accessory port of the endoscope.

3. The apparatus of claim 2 wherein the third segment has a third diameter greater than the second diameter, the proximal portion having a first transition portion extending proximally from the distal portion to the second segment and a second transition portion extending proximally from the second segment to the third segment.

4. The apparatus of claim 3 wherein the second segment has a length of between about 5 and 15 centimeters, the second segment being configured to adjacently extend through the accessory port of the endoscope to allow for collapse of the wire guide.

5. The apparatus of claim 3 wherein the first transition portion proximally tapers between the first and second diameters to the second segment and wherein the second transition portion proximally flares between the second and third diameters to the third segment of the wire guide.

6. The apparatus of claim 2 wherein the proximal portion has a first transition portion extending proximally from the distal portion to the second segment, the second segment extending proximally to the proximal end of the wire guide.

7. The apparatus of claim 6 wherein the first transition portion proximally tapers between the first and second diameters to the second segment.

8. The apparatus of claim 1 further comprising an outer coating disposed about the wire guide and along the distal and proximal portions so that the apparatus has a constant outer diameter therealong.

9. The apparatus of claim 8 wherein the outer coating comprises polytetrafluoroethylene, polyethylene, polypropylene, perfluoroelastomer, fluoroelastomer, nitrile, neoprene, polyurethane, silicone, styrene-butadiene, rubber, or polyisobutylene or a mixture thereof.

10. The apparatus of claim 1 wherein the distal portion extends for a length of about 160 and 185 cm from the distal end to the proximal portion and wherein the proximal portion comprises a first transition portion extending proximally from the distal portion to the second segment having a length of about 5 and 15 cm.

11. The apparatus of claim 1 wherein the distal portion extends at least partially beyond a distal end of the insertion tube.

12. The apparatus of claim 1 wherein the wire guide has a length of between 185 centimeters (cm) and 225 cm.

13. An endoscopic apparatus comprising:
an insertion tube for an endoscope configured for advancement into a patient, the insertion tube having an accessory port, the insertion tube extending distally from the accessory port to a distal tip:
a wire guide disposed through the insertion tube for delivery in the patient, the wire guide having a distal portion extending to a distal end and a proximal portion extending from the distal portion to a proximal end, the distal portion extending distally from the accessory port of the insertion tube in substantially the same direction as the distal tip of the insertion tube extends distally from the accessory port, the distal portion having a first segment and the proximal portion having a second and a third segment; the second segment being less rigid than the first segment, the second segment being made of material having increased flexibility, the second segment being located distant from the center of the wire guide, the third segment extending proximally from the second segment to the proximal end of the wire guide, the second segment being configured to allow the third segment of the proximal portion to droop when proximally extending through the accessory port of the endoscope as the distal end of the distal portion extends distally.

14. The apparatus of claim 13 wherein the material is superelastic material.

15. The apparatus of claim 13 wherein the material is a shape memory material.

16. An endoscopic apparatus comprising:
an insertion tube for an endoscope configured for advancement into a patient, the insertion tube having an accessory port, the insertion tube extending distally from the accessory port to a distal tip;
a wire guide disposed through the insertion tube for delivery in the patient, the wire guide having a distal portion extending to a distal end and a proximal portion extending from the distal portion to a proximal end, the distal portion extending distally from the accessory port of the insertion tube in substantially the same direction as the distal tip of the insertion tube extends distally from the accessory port, the proximal portion being less rigid than the distal portion, the proximal portion having a reduced diameter and extending proximally through the accessory port; the proximal portion being configured to droop relative to gravity when it proximally extends through the accessory port of the endoscope as the distal end of the distal portion extends distally.

17. The apparatus of claim 16 wherein the distal portion has a distal diameter and the proximal portion has a proximal diameter less than the distal diameter to allow the proximal portion to collapse when proximally extending through the accessory port of the endoscope.

18. The apparatus of claim 17 wherein the proximal portion has a transition portion extending proximally from the distal portion to the proximal portion.

19. The apparatus of claim 18 wherein the transition portion proximally tapers between the distal and proximal diameters to the proximal portion.

* * * * *